(12) United States Patent
Lerer

(10) Patent No.: US 9,874,499 B1
(45) Date of Patent: Jan. 23, 2018

(54) METHOD OF SAMPLE PREPARATION FOR EPIDERMAL NERVE FIBER DENSITY TESTING

(71) Applicant: Boaz Lerer, Phoenix, AZ (US)

(72) Inventor: Boaz Lerer, Phoenix, AZ (US)

( * ) Notice: Subject to any disclaimer, the term of this patent is extended or adjusted under 35 U.S.C. 154(b) by 83 days.

(21) Appl. No.: 15/136,255

(22) Filed: Apr. 22, 2016

Related U.S. Application Data

(60) Provisional application No. 62/151,590, filed on Apr. 23, 2015.

(51) Int. Cl.
*G01N 1/30* (2006.01)
*G01N 1/36* (2006.01)

(52) U.S. Cl.
CPC ............... *G01N 1/30* (2013.01); *G01N 1/36* (2013.01)

(58) Field of Classification Search
CPC ..................................................... G01N 1/00
See application file for complete search history.

(56) References Cited

U.S. PATENT DOCUMENTS

| | | | |
|---|---|---|---|
| 2,219,605 | A | 10/1940 | Henry |
| 3,515,128 | A | 6/1970 | Mcevoy |
| 4,734,192 | A | 3/1988 | Champion |
| 4,886,742 | A | 12/1989 | Kortright |
| 5,205,989 | A | 4/1993 | Aysta |
| 5,968,731 | A | 10/1999 | Layne |
| 6,309,605 | B1 | 10/2001 | Zermani |
| 6,613,756 | B2 | 9/2003 | Duncan |
| 8,516,909 | B2 | 8/2013 | Lihl |

*Primary Examiner* — Jyoti Nagpaul
(74) *Attorney, Agent, or Firm* — Venjuris, P.C.

(57) ABSTRACT

An improved method for staining biopsy samples taken from patients for epidermal nerve fiber density testing is described. The method employed in the present invention minimizes tissue damage incurred during biopsy sample processing for immunostaining and involves minimal handling of the sample. Moreover, the unique steps of covering wells that do not receive samples as well as novel labeling pattern of the patient samples significantly reduces the chances of making errors in mixing patient samples while processing a large batch of patient specimens.

8 Claims, 6 Drawing Sheets

| Case Accession Number | Patient Name | Biopsy Location | 96 Well Plate Color Code | Tech |
|---|---|---|---|---|
| xx-1 | Alpha | L/FT | Red | Smith |
| xx-1 | Alpha | L/CA | Blue | Smith |
| xx-1 | Alpha | L/DT | Green | Smith |
| xx-2 | Beta | R/CA | Pink | Smith |
| xx-2 | Beta | L/CA | Brown | Smith |
| xx-3 | Gamma | R/FT | Navy | Jones |
| xx-3 | Gamma | R/CA | Orange | Jones |
| xx-3 | Gamma | L/FT | Turquoise | Jones |
| xx-3 | Gamma | L/CA | Black | Jones |
| xx-4 | Delta | R/FT | Purple | Smith |
| xx-4 | Delta | R/CA | Lilac | Smith |
| xx-4 | Delta | R/FT | Lime | Smith |
| xx-4 | Delta | L/FT | Teal | Smith |
| xx-4 | Delta | L/CA | Yellow | Smith |

Fig. 1

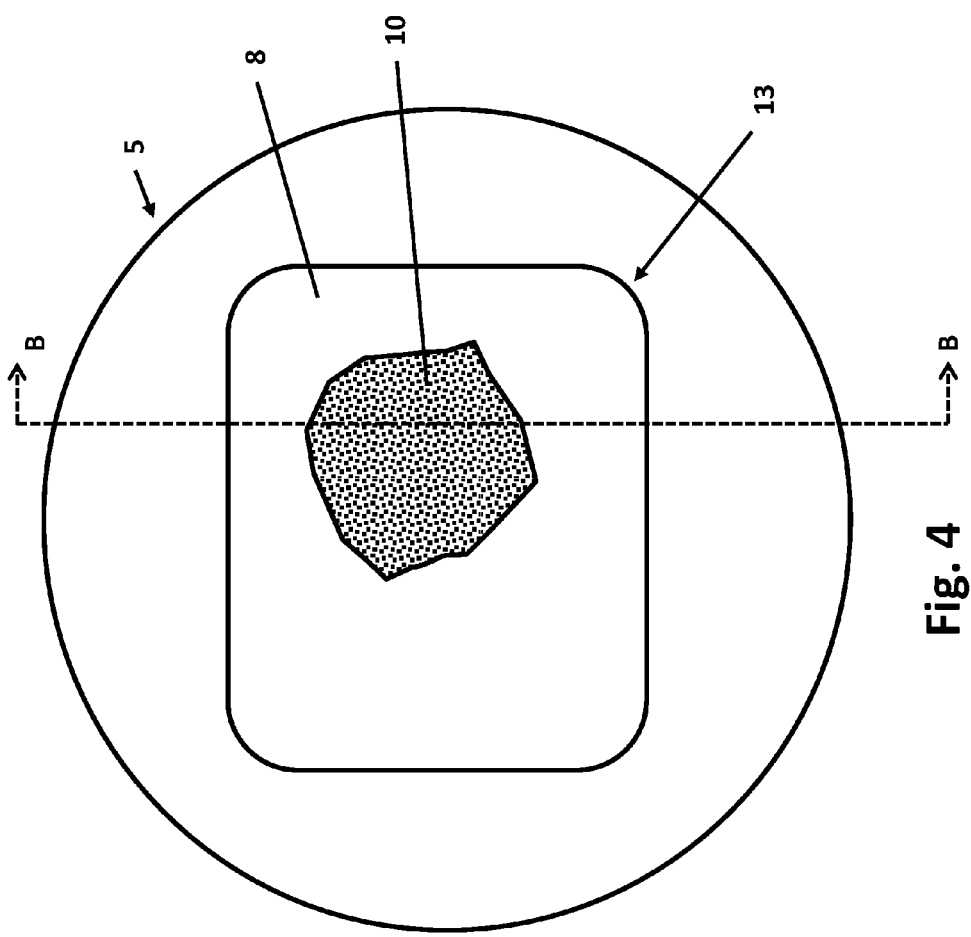
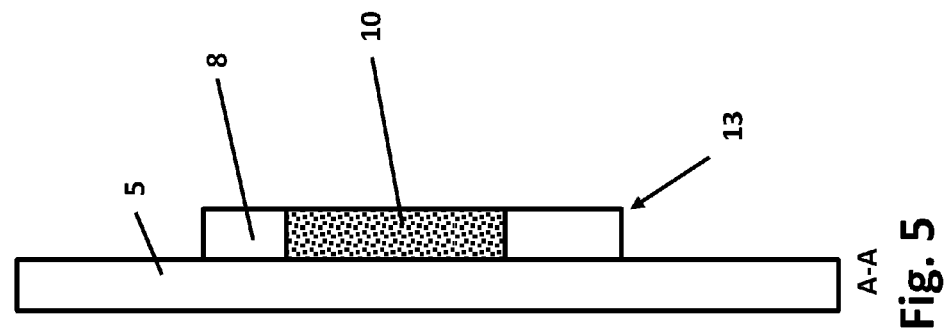

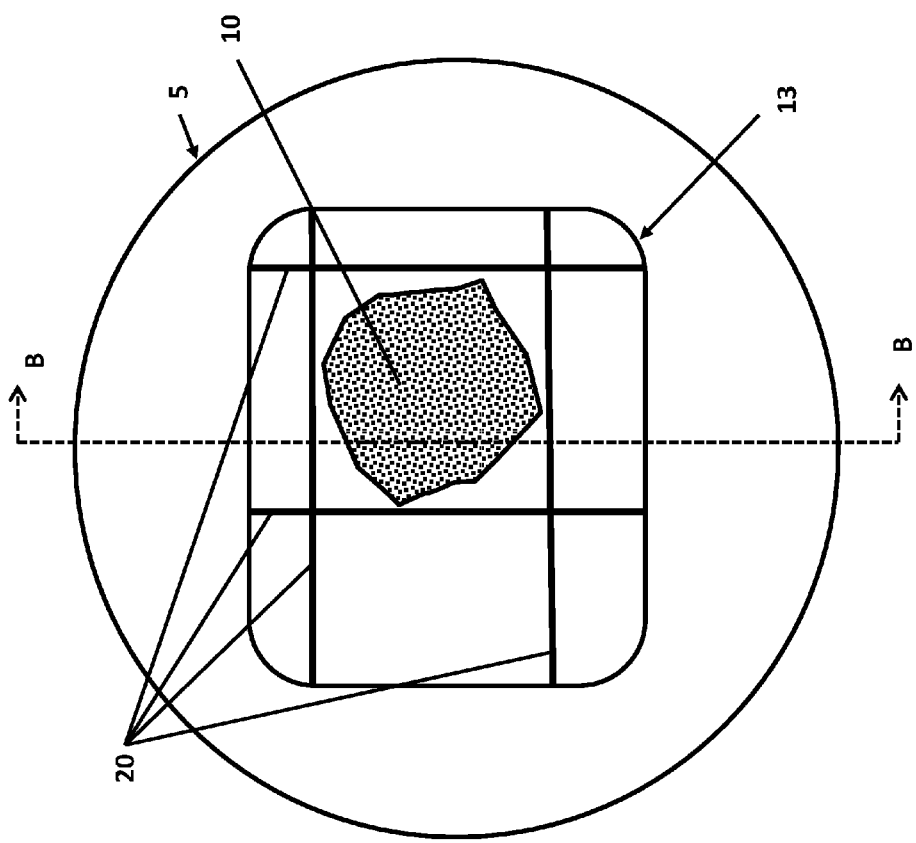
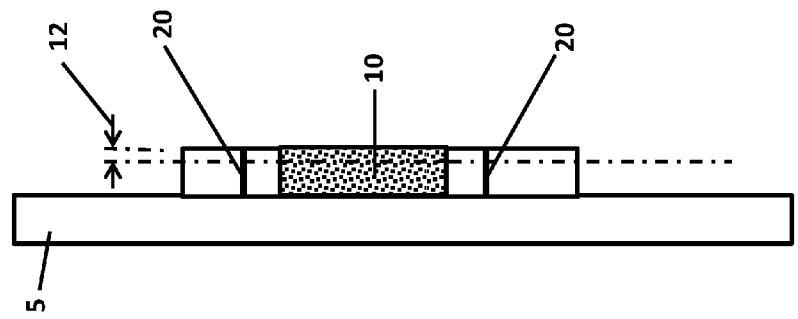
Fig. 6
Fig. 7

METHOD OF SAMPLE PREPARATION FOR EPIDERMAL NERVE FIBER DENSITY TESTING

CROSS REFERENCE TO RELATED APPLICATION

The present application claims priority of the United States Provisional Utility Patent Application entitled "Epidermal Nerve Fiber Density Test", having application No. 62/151,590 filed on Apr. 23, 2015 which is entirely incorporated herein by reference.

FIELD OF INVENTION

The present invention relates to the field of measuring epidermal nerve fiber density. More specifically, the invention provides a method for tissue preparation and staining of biopsy samples to determine nerve fiber density.

BACKGROUND

Damage to the small, unmyelinated fibers in the peripheral nerves that innervate the skin and internal organs causes Small Fiber Neuropathy (SFN). This peripheral nerve disease specifically affects small diameter nerve fibers. Symptoms of SFN include a decrease in the number, density and length of small nerve fibers in the epidermis of skin biopsy specimens. It is important to diagnose SFN since detection at an early stage can predict progression to a larger-spread neuropathy.

The first step in diagnosis of SFN is studying the history of the patient and physical examination that include a detailed review of symptoms, rate of progression, and complaints suggestive of autonomic fiber involvement. Another test to diagnose SFN is the Quantitative Sensory Testing (QST). QST provides a threshold for detection of thermal sensation, thermal pain and vibratory sensation. However, QST has a few limitations such as abnormalities in either the central nervous system or peripheral nervous system can result in the same deficit, inability to distinguish between feigned and true loss of sensation to name a few.

One of the highly specific and sensitive tests for SFN is the punch skin biopsy. A punch biopsy can be taken typically from the sites of interest in evaluation of SFN. Some of the common areas of interest are the proximal and distal arm, lateral distal leg, lateral proximal thigh, lateral distal thigh and dorsum of the foot.

Samples are sectioned and stained using immunohistochemistry. However, while working with large number of patient samples, chances of introducing human errors increases as sections get transferred for each step of immunoassay. In addition, tissue damage is introduced while transferring sections rendering the immunostained sample damaged and hence unusable for examining under the microscope in order to diagnose SFN.

SUMMARY

The present invention provides an improved method to prepare punch biopsy samples from patients for immunohistochemistry (IHC) for an epidermal nerve fiber density test (ENFD) for detecting SFN.

One aspect of this invention relates to a method of specimen preparation for cryostorage of the biopsy samples. The method includes fixing the biopsy samples in an appropriate fixative followed by addition of cryoprotectant. These samples are then frozen and stored in fridge at −4° C. for 24 hr.

Another aspect of the invention relates to a method of cryostorage to ensure efficient storage and retrieval of patient tissue samples for further analysis. The method includes appropriate labeling of samples for patient accession information, positioning of the biopsy in OCT, and freezing of samples for storage in the freezer.

Another aspect of the invention relates to a method of cryostat sectioning of the biopsy sample. The method includes transfer of the biopsy to cryostat, use heat extraction and freeze biopsy in cryostat, sectioning of the biopsy at appropriate thickness, transfer of biopsy to a 96 well plate that are appropriately labeled with patient identification for biopsy samples. This is followed by either proceeding to the next step of staining samples for immunohistochemistry or the 96 well plate with samples can be held in the freezer at −20° C. to −25° C. for processing at a later time period.

Another aspect of this invention relates to the method of staining samples for immunohistochemistry. This includes preparation of appropriate buffers and chemicals for immunostaining, rinsing the tissue in appropriate buffers and solutions, incubating in blocking solution, addition of primary antibodies, rinsing in appropriate buffers, addition of secondary antibodies, rinsing in appropriate buffer, followed by incubations in ABC solution and then SG solution interspersed with a rinse in appropriate buffers.

Another aspect of the invention relates to a method of mounting slides with antibody-stained biopsy sections for analysis. This method involves transferring of samples that are immunostained with appropriate antibodies as mentioned above on a slide labeled with patient details, followed by appropriate positioning of samples on slides, followed by counterstaining and dehydrating before placing a coverslip on the sample.

Pursuant to this invention, a 96 well plate is used for immunoassay wherein samples are not transferred from one well to the other for blocking, rinsing and antibody incubation steps. Samples processing takes place within the same well. Samples are processed and rinsed using millapore laboratory multiscreen HV pump. The pump is initiated to pull the liquid down and out of the wells. This procedure enables very minimal damage to the sections and enhances the quality of immunostaining as well as sample preparation.

A preferred embodiment of this invention comprises covering the wells that do not get the sections for staining with a tape. This step helps in keeping the samples organized as well as minimizes the chances of any human errors in mixing the sample numbers.

Another important embodiment of this invention comprises of color coding the wells that receive the patient samples with color assigned to the samples in the log book.

The present invention can have applicability for any other type of tissue sample preparation where the tissue sample needs to undergo minimal handling and damage while undergoing processing and/or staining for analysis.

BRIEF DESCRIPTION OF THE DRAWINGS

Embodiments of the disclosure will become more fully understood from the detailed description and the accompanying drawings, wherein:

FIG. 1 illustrates an embodiment of a patient labeling log;

FIG. 4 illustrates a front view of an embedded biopsy 13, which is a biopsy 10 encased and frozen in OCT 8 and then mounted on a chuck 5;

FIG. 5 illustrates section A-A of FIG. 4;

FIG. 6 illustrates a front view of embedded biopsy 13 with razor incisions 20 made around the biopsy 10;

FIG. 7 illustrates section B-B of FIG. 6

DETAILED DESCRIPTION OF THE PREFERRED EMBODIMENTS

Figure 2:
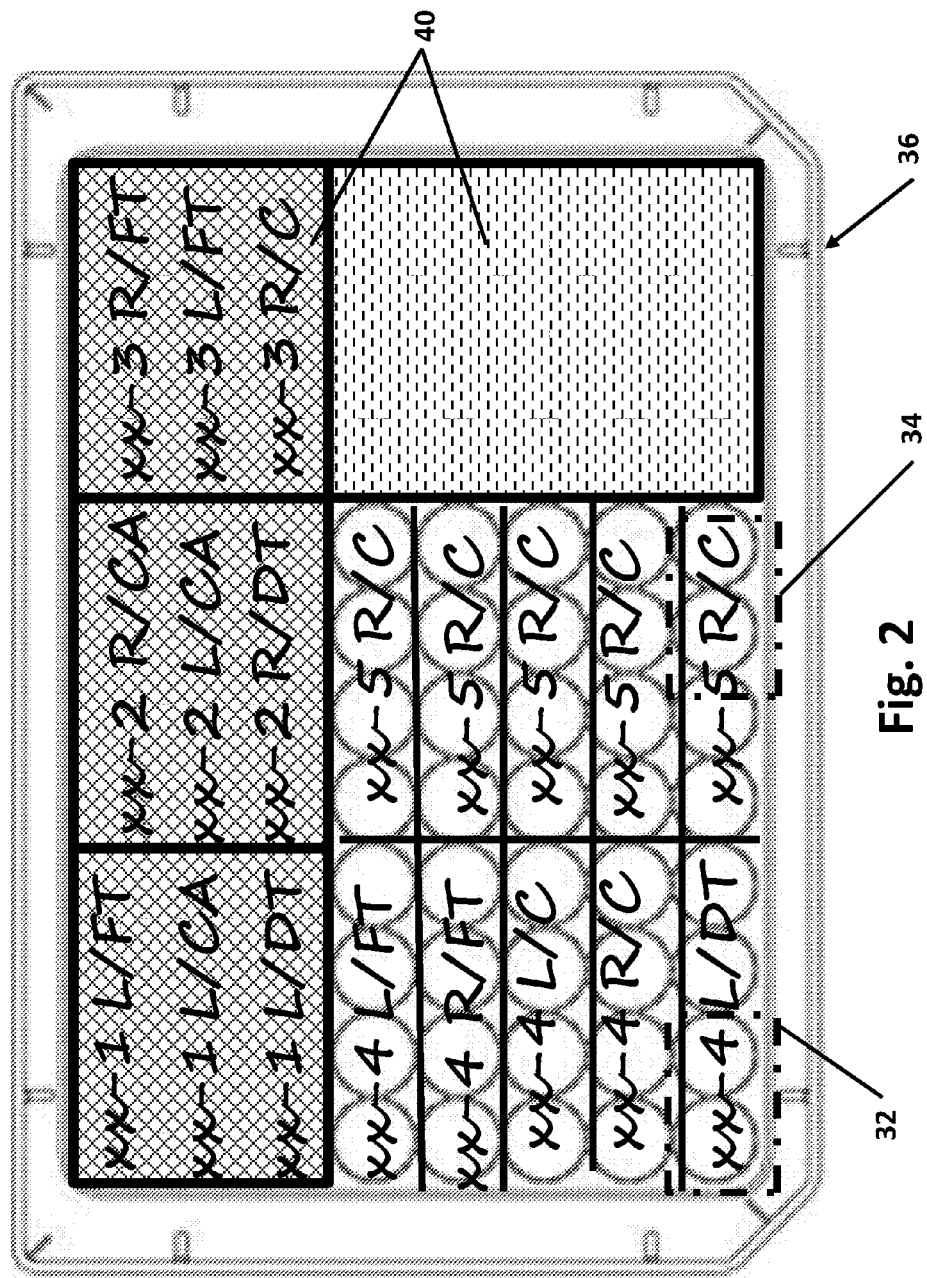
FIG. 2 illustrates an embodiment of top view of a lid fitted on a 96 well plate labeled with patient biopsy samples and with tape covering non-used wells.

Unless otherwise defined, all technical and scientific terms used herein have the same meaning as commonly understood by one of ordinary skill in the art. To test this invention, methods and materials similar or equivalent to those described herein can be used. The materials, methods, and examples are illustrative only and are not intended to be limiting.

Specimen preparation entails placing Zamboni's fixative vials per case with tissue on holding block wherein patient's name, biopsy locations and time of placing punch biopsy tissue in fixative are verified. The biopsy cassettes with case number are labeled and information is logged into the Patient log accordingly. Punch biopsy 10 is submerged in Zamboni's fixative for no less than 18 hr and no more than 24 hr. Following Zamboni's fixation, punch biopsy 10 is rinsed in its vial with PBS buffer two times. After rinsing punch biopsy 10, appropriate cryoprotectant such as sucrose buffer is added and the punch biopsy 10 is placed in the holding block and stored in fridge at −4° C. for 24 hr.

Enough optimal cutting temperature (OCT) compound 8 is used to cover bottom only of clear biopsy cassette. Punch biopsy 10 is oriented in cassette with the skin surface facing case number and patient name. If punch biopsy 10 is folded or flat, bottom of clear biopsy cassette is covered with OCT compound 8 and placed in Microtome on freeze plate. As soon as OCT compound 8 is no longer clear, it is removed from Microtome and punch biopsy 10 is placed in cassette, skin surface facing case number and patient name. Fine tip forceps are used to help keep punch biopsy 10 standing straight. This is then placed back on freeze plate until punch biopsy 10 is frozen in OCT 8 to obtain an embedded biopsy 13. Once frozen, add enough OCT 8 to fill cassette. Place cassette in freezer in a tray for 20 minutes until completely frozen.

Samples are then prepped for cryostat sectioning. Embedded biopsy 13 in clear cassettes are retrieved from freezer. Starting with the first case number, place a chuck 5 on the freeze plate and apply some OCT compound in the middle of the chuck. Once the OCT compound begins to turn white, immediately take embedded biopsy 13 out of cassette, turn it over and place on chuck with the same orientation as it was in cassette. The bottom of the embedded biopsy 13 (flat side) should now be face up on the chuck 5. Move the freeze bar over, lower onto biopsy and tighten into place. After 3 minutes, freezer bar is removed. Place chuck 5 with skin surface facing the cutting edge and lock into place for cutting.

Initially, the face of the embedded biopsy 13 is sliced parallel to the face of the chuck, preferably at a depth 12 of 8 microns, but a depth 12 between 4 and 40 microns will also work. See, FIG. 7. The purpose of this initial slicing is to expose a face of the biopsy 10.

Figure 8:
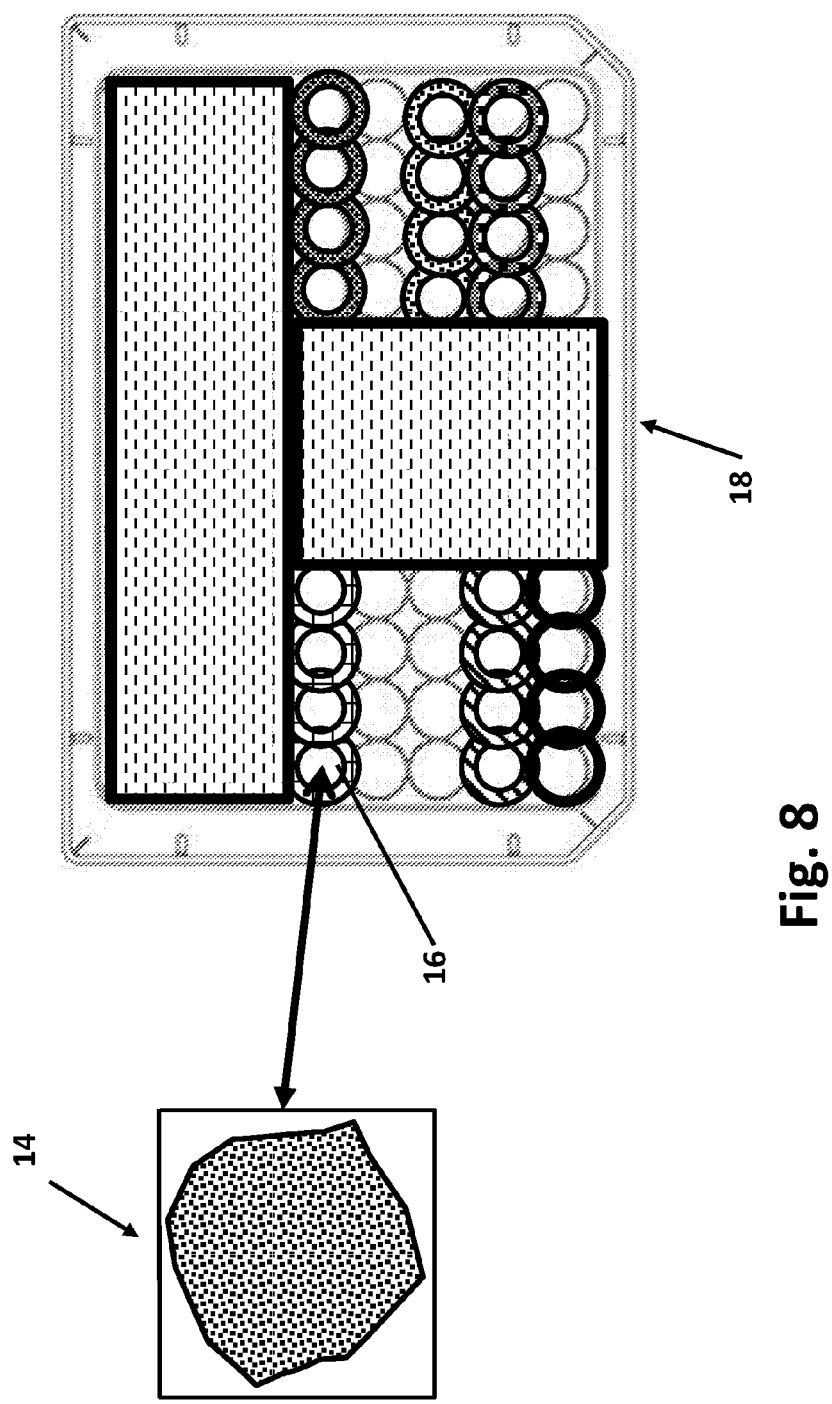
FIG. 8 illustrates a 50 micron sample 14 taken off the chuck 5 and placed into a well 16 of a 96-well plate 18.

Next, embedded biopsy 13 should be prepped for making biopsy samples, preferably having a thickness of 50 microns, for transferring to a 96 well plate. This step for prepping embedded biopsy 13 involves using a blade to carefully make incisions 20 around the biopsy to trim embedded biopsy 13. The incisions are made perpendicular to the chuck 5 as shown in FIGS. 7 and 8. The purpose of these perpendicular incisions is so that when further slices are taken parallel to the chuck, the excess OCT falls away and the remaining sample 14 can fit into a 96-well plate.

The number of incisions 20 may vary according to the protocol. As shown in FIG. 6, it is preferred to make a total of four incisions 20 in a square pattern around the embedded biopsy 13. But other shapes and cuts could be used. For example a circular plug cutter could be used; or, the cuts could be made in a triangular or other geometric shape.

Regardless of the shape, caution should be taken as not to cut the biopsy 10 with the razor. The trimming should be close enough to the biopsy 10 to be able to place the sample 14 into a well 16 of a 96-well plate 18.

The embedded biopsy 13 is then again sliced parallel to the face of the chuck 5. The preferred thickness of this slice is 50 microns, but a range of 30 to 70 microns would also work. When the slice is made, the sample 14 is picked and placed into a well 16 using forceps and brush. The excess OCT 8 from the embedded biopsy 13 can be discarded.

Continue cutting sections 14, preferably at a thickness of 50 microns, until row wells A&B are filled for the first biopsy in the case. Similar process is repeated for the second biopsy and so on until all biopsies in the case are cut. The razor blade will be used several times during cutting to keep the square around the biopsy. When moving onto the next case, it is preferred to set the slicing/cutting depth back to 8 microns to begin the process again. After one case is completed, add one drop of antifreeze to each well. Put lid on tray and place in freezer.

As cases are being completed, turn chuck with embedded biopsy 13 upside down in respective clear biopsy cassette and keep in cryostat in order. Once all cases are complete, take samples to sink area (carefully to not drop cases or they will be mixed up) and cover bottom of cassette with OCT 8, carefully run chuck under water to loosen embedded biopsy 13 and take off chuck. Place embedded biopsy 13 in cassette, biopsy 10 side down and put back in freezer.

Immunostaining of sample 14 are carried out in the 96 well plates equipped with suctioning capacity. These plates are prepared for processing the sample and are labeled for an efficient immunostaining protocol.

As seen in FIG. 1, patient biopsy 10 information is recorded in a log 30 and the corresponding sample 14 is assigned a color. All the samples obtained from the same patient are assigned the same color.

Labeling of 96 well plates 18 are done by checking the accession files and the patent biopsy log.

Once the patient information is verified, the case accession number 32 and their biopsy locations 34 are written down on the lid 36 of the 96 well plate as seen in FIG. 2. For example, in a brand new plate, for the first patient, 4 samples obtained from SP15-00001R/Calf would go in wells A1-A4. The next 4 samples obtained from the same patient's other location, L/Calf will go in wells A5-A8.

Figure 3:
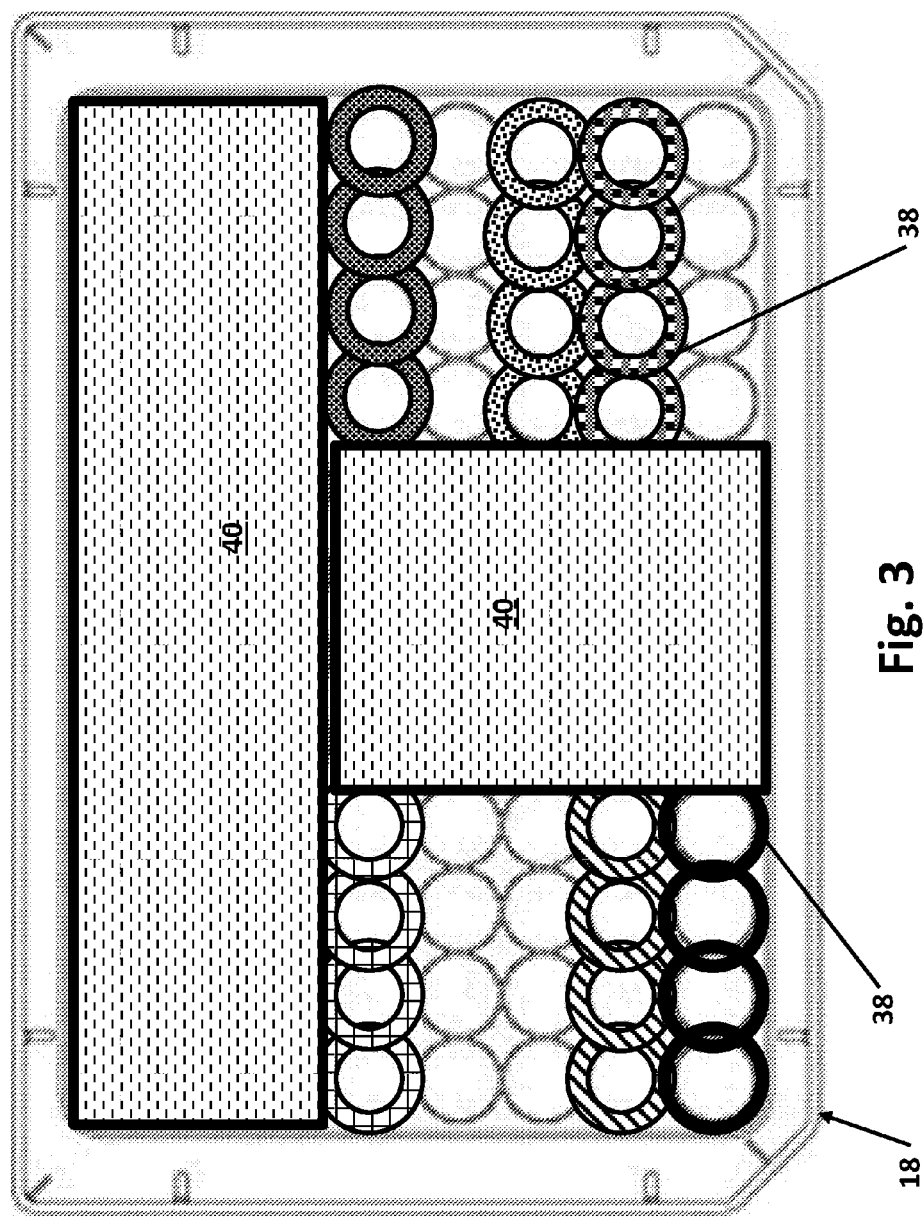
FIG. 3 illustrates a top view of a 96 well plate marked with colors around wells corresponding to the patient labelling scheme of FIG. 1 and with tape covering non-used wells.

The lid 36 is then taken off and the outer rim 38 of the well is colored as seen in FIG. 3 based on the color assigned to the patient in the log 30. A felt tip marker is preferred but other known marking methods, such as stickers or paint, will also work. Wells 16 that do not receive patient tissue samples are taped with a non-transparent tape 40, like duct tape, for example.

Samples are added in a similar fashion on the rows below, from B1 to B8 for the next patient. The entire plate is mapped out in a clear schematic. These microscreen plate wells are used for one time use only and the plate itself is reused multiple times.

Wells that do not have tape 40 covering them are filled with 100 microliters of TBS buffer using a multi-channel pipette.

Samples for staining are selected in a certain order wherein, no two adjacent sections are pulled. Ideally similar set of samples would be pulled from both locations for the same patient. For example, 6th and 12th sample will be pulled from the R/Calf sample and 6th and 12th sample will be pulled from the L/Calf sample. Preferably samples are selected for staining by observing under a dissecting microscope for any tears and damages to the samples that can interfere with the final results.

Samples are primarily analyzed to identify intact tissues. With the lid 36 off and the magnification set to maximum, the epidermis is examined and the area of tissue beneath it is checked for any abnormalities. The epidermal/dermal junction is where the small fibers that are stained and then subsequently examined/counted by the pathologist are found. It is important to only pull samples that have an intact and complete epidermis for staining (no shredding/tears and tiny ones should be avoided if larger ones are available). Sample numbers are logged in the log book.

For transferring the sample, a Ted Pella 1.5 mm nichrome transfer loop is preferably used. The samples are carefully picked up, trying to avoid ripping the dermal tail off, and placed in their corresponding well(s) in multiscreen HV plate. Once the immuno run is started, the samples should be kept submerged and not allowed to float or dry out. The sample can be watched through dissecting microscope to determine whether it falls off loop. The sample can be seen to come off and go beneath the surface of the buffer. Continue filling up the multiscreen HV plate until it is completely filled and ready to be initiated in the immunorun.

Sample 14 is processed for immunostaining with various antibodies as well as other staining protocols.

During the processing of samples for immunostaining, samples are retained in the same well and not transferred to a different well for subsequent steps in the procedure. The 96 well microwell plate equipped with suctioning capacity is attached to the vacuum manifold to suction out excessive liquids/buffers during subsequent rinses.

To perform an immunoassay using the compositions of the present inventions a sample can be first contacted with a blocking solution followed by primary antibody composition, i.e., containing primary antibodies in blocking solution. This is followed by multiple rinses in appropriate buffer and solutions to get rid of unbound primary antibodies, the sample is then contacted with secondary antibody composition, i.e., containing secondary antibodies coupled to detectable moieties in blocking solution.

A preferred embodiment of this immunoassay would contain the primary antibody composition with a full strength blocking solution comprising of 0.05 g of Powdered Milk, 1 ml of 1% Triton X-100 (1.0 ml Triton X-100/99 ml TBS), 8.6 ml of 1×TBS Buffer and 0.4 ml (400 ul) of Normal Goat Serum. Appropriate amount of primary antibodies are added to the blocking solution. This solution is added to the samples in the 96 well plate.

In a further embodiment of the immunostaining method of the present invention, samples are rinsed using millapore laboratory multiscreen HV pump. The pump is initiated to pull the liquid down and out of the wells. The samples should now stick to the bottoms; however, in rinsing they can sometimes climb back up or stick to the sides of the well. The samples are rinsed again by using 100 ul of the same 1×TBS buffer as before. Continue to rinse until the potassium permanganate incubation (100 ul per well for 15 minutes on the shaker). Melanin inside the tissue will bleach, and turn brown. The samples are rinsed with 1×TBS three or four times. The samples need to be at the bottom of the wells, since this will be the last time they will be visible until the end of day 2. If any are clinging to the sides, a disposable pipette and TBS can be used to gently get it down.

Rinsing can be paused at this stage for an incubation in oxalic acid for three and a half minutes. It is very important to not let this incubate longer than 5-10 minutes. The samples will look clear again, since this step acts as a decolorizer, it is also quite harsh on the tissue if left unchecked and rinsed in time. Resume rinsing several more times with care not to agitate too hard.

The blocking solution is pulled off by using the filter plate/multiscreen HV pump and placed in 100 ul of primary antibodies on each well. The plate is carefully set on the shaker overnight. Make sure the bottom of the plate and the top of the shaker are both dry, otherwise liquid can leak out overnight. The lids are covered and left on the shaker overnight.

In further embodiments of immunostaining method of the present invention, samples are rinsed with 100 ul of 1×TBS several times. Secondary antibodies composition is added to the samples and set on shaker for approximately one hour.

A preferred embodiment of this immunoassay would contain the secondary antibody composition with a full strength blocking solution comprising of 0.05 g of Powdered Milk, 1 ml of 1% Triton X-100 (1.0 ml Triton X-100/99 ml TBS), 8.6 ml of 1×TBS Buffer and 0.4 ml (400 ul) of Normal Goat Serum. Appropriate amount of secondary antibodies are added to the blocking solution. This solution is added to the samples in the 96 well plate.

In further embodiment of the antibody staining method of the present invention, samples incubated in secondary antibodies for an hour are rinsed with TBS buffer multiple times. This is followed by incubation of the samples in methanol peroxide for 30 minutes to block endogenous peroxidase.

A preferred embodiment of this immunoassay would contain methanol peroxide in a proportion comprising of approximately 6.7 ml of 1×PBS Buffer, 3 ml of Methanol, and 0.33 ml of 30% Hydrogen Peroxide. Methanol peroxide would be preferably prepared 10 minutes prior to incubation.

In further embodiment of the antibody staining method of the present invention, samples incubated in methanol peroxide for 30 minutes are rinsed with PBS buffer multiple times. This is followed by incubation in Vector ABC working solution for one hour.

A preferred embodiment of this immunoassay would contain Vector ABC working solution in a proportion comprising of approximately 2000 ul of 1×PBS, with reagents from Vector ABC kit as per the specifications on the kit. Vector ABC working solution would be preferably prepared and mixed for 30 minutes prior to incubation.

In further embodiment of the antibody staining method of the present invention, samples incubated in Vector ABC working solution for 30 minutes are rinsed with PBS buffer multiple times. This is followed by incubation in Vector SG working solution also called as Chromagen solution for one three and a half minutes. The plate is preferably covered for incubation in the dark. At the end of the three and a half minute incubation, the tissue will appear blue/black. The samples are rinsed with PBS buffer several times.

A preferred embodiment of this immunoassay would contain Chromagen working solution in a proportion comprising of approximately 2000 ul of 1×PBS, with reagents from Vector SG kit as per the specifications on the kit.

The samples are mounted on slides with proper precautions to ensure that the tissue sections do not dry out.

Protocol for immunoassay as well as staining samples may vary slightly.

EXAMPLE

Immunoassay for staining with PGP 9.5 antibody would comprise the following steps on the 50 micron samples in the wells. For each of these steps mentioned below, after completion of each incubation, liquid is aspirated using millapore laboratory multiscreen HV pump. The pump is initiated to pull the liquid down and out of the wells.
1. Samples are rinsed in TBS buffer for 10 minutes (two times).
2. Samples are incubated in 0.25% potassium permanganate for 15 minutes.
3. Samples are rinsed in TBS for 10 minutes.
4. This is followed by incubation with 5.0% oxalic acid for 2 to 5 minutes.
5. Samples are rinsed in TBS for 10 minutes.
6. Samples are incubated in blocking buffer, preferably 4.0% NGS blocking solution for one to two hours.
7. Samples are incubated with primary antibodies (appropriate concentration as per the manufacturer's instructions) overnight.
8. Samples are rinsed in TBS buffer for 10 minutes (two times).
9. Samples are incubated with secondary antibodies (appropriate concentration as per the manufacturer's instructions) for one hour.
10. Samples are rinsed in TBS buffer for 10 minutes (two times).
11. This is followed by an incubation with 30% methanol in PBS and 1% hydrogen peroxide for 30 minutes to minimize background staining.
12. Samples are rinsed in PBS buffer for 5 minutes (two times).
13. This is followed by incubation in ABC solution for one hour
14. Samples are rinsed in PBS buffer for 10 minutes (two times).
15. The next step comprises of incubation in SG solution for an average of 10 minutes.
16. Samples are rinsed in PBS for 10 minutes (two times) before mounting them on slides for viewing.

Protocol for staining and mounting samples for non-immuno assays are as follows:

Example: H&E and Congo Red Staining and Mounting

Samples picked for this staining should preferably have an intact epidermis and a full shape. Nonconsecutive sections are picked and preferably the ones further apart are picked to see the variety of tissue morphology for diagnoses. For example, $3^{rd}$ and $9^{th}$ section from R/Calf and $3^{rd}$ and $9^{th}$ section from L/Calf
1. Two tissue samples are picked and wet mounted on a slide one above the other.
2. Samples are allowed to air dry in a slide rack to enable adhering to the slide for staining steps.
3. Samples are stained for H&E and for Congo red as per the manufacturers instructions.
4. Stained samples are mounted on slides in a drop of water. Sections are positioned for correct orientation and laid flat on the slide.
5. Samples are then allowed to air dry on the slides.
6. Slides with dried samples are immersed in staining receptacles filled with water. This enables removing of excess stain on the samples.
7. These slides are then cover slipped and ready for microscopy.

While embodiments of the disclosure have been described in terms of various specific embodiments, those skilled in the art will recognize that the embodiments of the disclosure may be practiced with modifications within the spirit and scope of the claims.

What is claimed is:

1. A method for preparation of tissues for detecting epidermal nerve fiber density, said method comprising the steps of:
    fixing an embedded biopsy in a chuck, the chuck having a first face;
    trimming the embedded biopsy by making an incision around the embedded biopsy with a blade, the direction of the incision being perpendicular to the first face, and the incision having an incision depth;
    slicing the embedded biopsy parallel to the first face, the slicing having a thickness less than the incision depth to create a trimmed sample for a well of a multi-well well plate, and
    transferring the trimmed sample to a well of the multi-well well plate for testing epidermal nerve fiber density.

2. The method of claim 1, wherein the slicing has a thickness within a range of 30-70 microns.

3. The method of claim 1, wherein the multi-well well plate is equipped with suctioning capacity.

4. The method of claim 1, further comprising the step of repeating the trimming, slicing and transferring steps until at least four samples have been transferred to four consecutive wells of the multi-well well plate.

5. The method of claim 1, further comprising the step of outlining a rim of each of the four consecutive wells with a color, the color corresponding to a predefined patient-color association.

6. The method of claim 1, further comprising the step of marking the lid of multi-well well plate with patient information over the location of four samples in the multi-well well plate.

7. The method of claim 1 further comprising the step of taping of the wells in the multi-well well plate that do not receive any samples with a non-transparent tape.

8. The method of claim 1 further comprising the step of rinsing the samples in the multi-well well plate using a vacuum manifold.

* * * * *